US010151730B2

(12) United States Patent
Reitmeier et al.

(10) Patent No.: US 10,151,730 B2
(45) Date of Patent: Dec. 11, 2018

(54) METHOD AND APPARATUS FOR DETERMINING A CONCENTRATION OF A CONSTITUENT OF A FLUID MIXTURE IN A FLUID CHAMBER

(71) Applicant: Continental Automotive GmbH, Hannover (DE)

(72) Inventors: Torsten Reitmeier, Wackersdorf (DE); Stephan Heinrich, Pfeffenhausen (DE); Sabrina Kolbeck, Eschlkam (DE)

(73) Assignee: CONTINENTAL AUTOMOTIVE GMBH, Hanover (DE)

( * ) Notice: Subject to any disclaimer, the term of this patent is extended or adjusted under 35 U.S.C. 154(b) by 68 days.

(21) Appl. No.: 15/127,201

(22) PCT Filed: Jul. 3, 2015

(86) PCT No.: PCT/EP2015/065261
§ 371 (c)(1),
(2) Date: Sep. 19, 2016

(87) PCT Pub. No.: WO2016/005293
PCT Pub. Date: Jan. 14, 2016

(65) Prior Publication Data
US 2017/0168019 A1    Jun. 15, 2017

(30) Foreign Application Priority Data
Jul. 8, 2014 (DE) .................. 10 2014 213 216

(51) Int. Cl.
*G06F 11/30* (2006.01)
*G01N 29/024* (2006.01)
(Continued)

(52) U.S. Cl.
CPC ....... *G01N 29/024* (2013.01); *G01N 29/2406* (2013.01); *G01N 29/348* (2013.01);
(Continued)

(58) Field of Classification Search
CPC .................................................. G01N 29/024
See application file for complete search history.

(56) References Cited

U.S. PATENT DOCUMENTS 6,487,916 B1 * 12/2002 Gomm ................ G01F 1/667
73/861.27
6,991,607 B2 * 1/2006 Muz .................... A61B 5/0836
600/531

(Continued)

FOREIGN PATENT DOCUMENTS

| CN | 103403506 A | 11/2013 | ........... G01F 23/296 |
| DE | 2945172 A1 | 5/1981 | ........... G01N 29/024 |

(Continued)

OTHER PUBLICATIONS

German Office Action, Application No. 102014213216.9, 4 pages, dated Mar. 4, 2015.
(Continued)

*Primary Examiner* — Phuong Huynh
(74) *Attorney, Agent, or Firm* — Slayden Grubert Beard PLLC

(57) ABSTRACT

The present disclosure relates to sensors and the teachings may be applied to a method and a corresponding apparatus for determining a concentration of a constituent of a fluid mixture in a fluid chamber. A method may include sending and receiving a first sound signal; sending and receiving a second sound signal; measuring the propagation time of the sound signals; calculating a value based on the propagation times representative of the concentration; sending and receiving a third sound signal with a second sound conversion unit; measuring a third propagation time; and calculating a second characteristic value based on the first propagation time and the third propagation time, representative of a mass flow of the fluid mixture.

9 Claims, 4 Drawing Sheets

(51) Int. Cl.
*G01N 29/24* (2006.01)
*G01N 29/34* (2006.01)

(52) U.S. Cl.
CPC .................. *G01N 2291/011* (2013.01); *G01N 2291/0215* (2013.01); *G01N 2291/02809* (2013.01); *G01N 2291/105* (2013.01)

(56) References Cited

U.S. PATENT DOCUMENTS

| | | | |
|---|---|---|---|
| 2003/0150262 A1 | 8/2003 | Han et al. | 73/152.18 |
| 2011/0314897 A1 | 12/2011 | Schellekens et al. | 73/23.3 |
| 2014/0041442 A1 | 2/2014 | Heinrich et al. | 73/61.79 |

FOREIGN PATENT DOCUMENTS

| | | | | |
|---|---|---|---|---|
| DE | 3544786 A1 | 6/1987 | ........... | G01N 29/024 |
| DE | 19841154 A1 | 4/2000 | ............... | G01F 1/66 |
| DE | 10228497 A1 | 1/2004 | ............... | A61B 5/083 |
| EP | 1624300 A1 | 2/2006 | ............... | B01D 1/00 |
| WO | 2016/005293 A1 | 1/2016 | ........... | G01N 29/024 |

OTHER PUBLICATIONS

International Search Report and Written Opinion, Application No. PCT/EP2015/065261, 25 pages, dated Sep. 28, 2015.
Chinese Office Action, Application No. 201580015969.9, 14 pages, dated Jul. 4, 2018.

\* cited by examiner

METHOD AND APPARATUS FOR DETERMINING A CONCENTRATION OF A CONSTITUENT OF A FLUID MIXTURE IN A FLUID CHAMBER

CROSS-REFERENCE TO RELATED APPLICATIONS

This application is a U.S. National Stage Application of International Application No. PCT/EP2015/065261 filed Jul. 3, 2015, which designates the United States of America, and claims priority to DE Application No. 10 2014 213 216.9 filed Jul. 8, 2014, the contents of which are hereby incorporated by reference in their entirety.

TECHNICAL FIELD

The present disclosure relates to sensors and the teachings may be applied to a method and a corresponding apparatus for determining a concentration of a constituent of a fluid mixture in a fluid chamber.

BACKGROUND

DE 35 44 786 A1 describes an arrangement for determining the concentration of gases by exploiting the dispersion of the velocity of sound, in which the phases of the two different measurement frequencies are directly compared with each other in the phase detector and the phase difference is used as a measure of the gas concentration.

US 2011/0314897 A1 describes a sensor chip for gas, which comprises cells for transmitting and receiving ultrasound and is designed to cover a broad range of frequencies and to measure a concentration of at least one gas component based on at least two responses within the range.

DE 29 45 172 A1 describes a method for determining the concentration of a gas, in particular the carbon dioxide content, in a gas mixture, wherein the sharply modified sound velocity of the gas in a dispersion area is used for determining the gas content by means of dispersion measurements on the gas mixture.

U.S. Pat. No. 6,487,916 B1 describes a method for determining a flow velocity of a fluid. A fluid is provided, which flows in a given direction. A first pulse is sent perpendicular to the given direction over a first known distance within the fluid and received. A second pulse is sent at an oblique angle to the given direction over a second known distance within the fluid and received. The respective speeds of the first and second pulses and their difference are determined. The difference is used to determine the flow velocity. The flow velocity is compared with a target flow speed.

SUMMARY

The teachings of the present disclosure may be applied to a method and a corresponding apparatus for determining a concentration of a constituent of a fluid mixture in a fluid chamber that contributes to the objective of reliably determining a concentration of the constituent. Some embodiments may include a method and a corresponding apparatus which facilitates a simultaneous determination of a mass flow.

In some embodiments, a method for determining a concentration of a constituent (B) of a fluid mixture (FG) in a fluid chamber (FR), may include a first sound conversion unit is operated for sending and receiving a first sound signal (SS1) at a predefined first frequency (F1) and for sending and receiving a second sound signal (SS2) at a predefined second frequency (F2), a first propagation time (L1) of the first sound signal (SS1) is determined and a second propagation time (L2) of the second sound signal (SS2) is determined, on the basis of the first propagation time (L1) and the second propagation time (L2), a first characteristic value (K1) is determined, which is representative of the concentration of the constituent (B) of the fluid mixture (FG), a second sound conversion unit is operated for sending and receiving a third sound signal (SS3) at a predefined third frequency (F3), a third propagation time (L3) of the third sound signal (SS3) is determined, and on the basis of the first propagation time (L1) and the third propagation time (L3), a second characteristic value (K2) is determined, which is representative of a mass flow of the fluid mixture (FG).

In some embodiments, the first characteristic value (K1) is representative of a carbon dioxide concentration in the fluid chamber (FR).

In some embodiments, an intake tract of a combustion engine comprises the fluid chamber (FR).

In some embodiments, the fluid chamber (FR) is arranged in the intake tract downstream of a junction with an exhaust gas recirculation unit.

Some embodiments may include an apparatus for determining a concentration of a constituent (B) of a fluid mixture (FG) in a fluid chamber (FR), comprising a first sound conversion unit which is designed for sending and receiving a first sound signal (SS1) and a second sound signal (SS2), a second sound conversion unit which is designed for sending and receiving a third sound signal (SS3) and a control unit which is designed for carrying out a method as described above.

In some embodiments, the first sound conversion unit comprises at least one first sound transducer (SW1).

In some embodiments, the at least one first sound transducer (SW1) is designed as a CMUT.

Some embodiments may include a reflector element (R), which is designed to reflect the first sound signal (SS1) and the second sound signal (SS2) in each case in such a way that the first sound conversion unit receives the reflected first sound signal (SS1) and the reflected second sound signal (SS2).

In some embodiments, the second sound conversion unit comprises at least one second sound transducer (SW2).

In some embodiments, the at least one second sound transducer (SW2) is designed as a CMUT.

BRIEF DESCRIPTION OF THE DRAWINGS

Exemplary embodiments of the invention are described in more detail below by reference to the schematic drawings. Shown are:

FIG. 4b a frequency spectrum of the first module in accordance with FIG. 4a,

FIG. 5b a frequency spectrum of the second module in accordance with FIG. 5a,

Elements of the same design or function are labelled with the same reference numeral across all figures.

DETAILED DESCRIPTION

Figure 1:
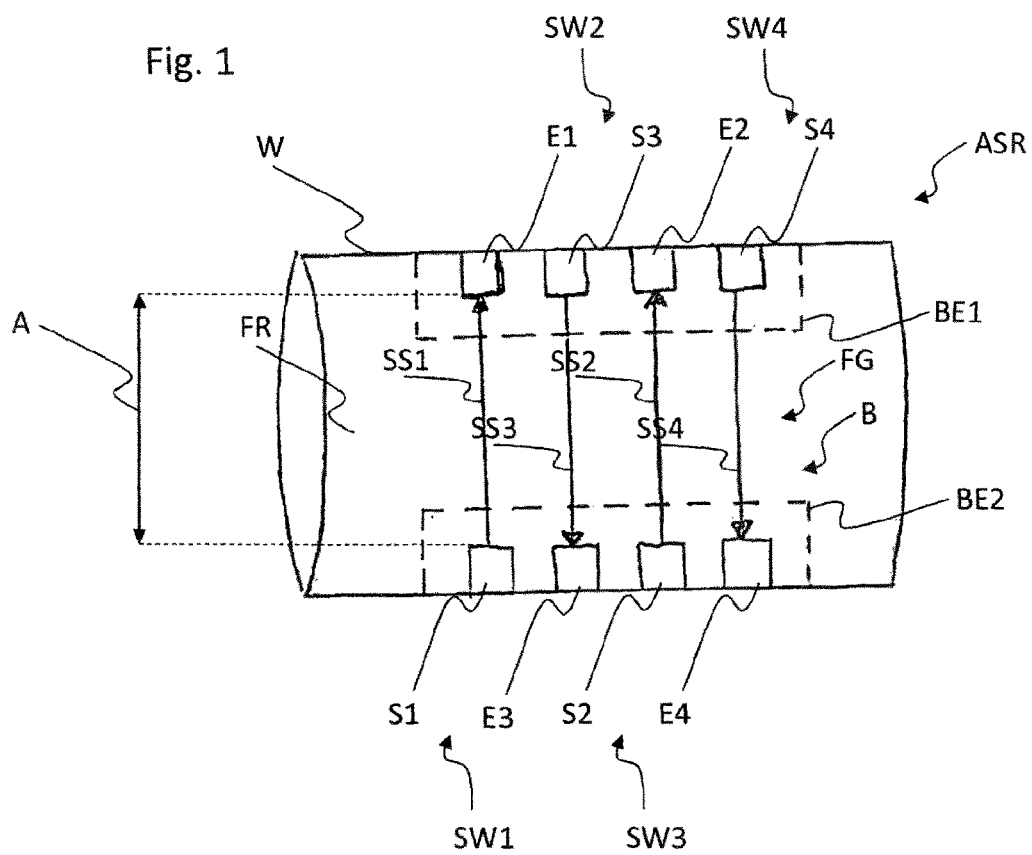
FIG. 1 a first exemplary embodiment of an apparatus for determining a concentration of a constituent of a fluid mixture in a fluid chamber, according to teachings of the present disclosure.

Some embodiments may include a method for determining a concentration of a constituent of a fluid mixture in a fluid chamber, in which a first sound conversion unit is operated for sending and receiving a first sound signal at a predefined first frequency and for sending and receiving a second sound signal at a predefined second frequency.

A first propagation time of the first sound signal is determined and a second propagation time of the second sound signal is determined. On the basis of the first propagation time and the second propagation time, a first characteristic value is determined, which is representative of the concentration of the constituent of the fluid mixture.

A dependency of a sound velocity of a sound signal on a frequency of the sound signal can also be designated as sound dispersion. In this connection, use is made of the fact that a sound dispersion effect depends on the fluid mixture and on a concentration of the constituent in the fluid mixture. This enables a reliable method for determining the concentration of the constituent in the fluid mixture, for example substantially independently of a mass flow of the fluid mixture. In addition, an apparatus for carrying out the method is robust and inexpensive to produce.

For this purpose, the first frequency is unequal to the second frequency.

In some embodiments, the first characteristic value is representative of a carbon dioxide concentration in the fluid chamber. In particular in cases where the carbon dioxide concentration is high, the effect of the sound dispersion is particularly marked.

In some embodiments, an intake tract of a combustion engine comprises the fluid chamber. A reliable and inexpensive exhaust gas recirculation is thus facilitated in an advantageous manner, since a determination of the carbon dioxide concentration based on ultrasound by means of sound dispersion is more reliable, for example, than a temperature-dependent, non-robust measurement of an oxygen concentration using a lambda probe. In addition, to determine the carbon dioxide concentration the use of a heater is merely optional.

In some embodiments, the fluid chamber is arranged in the intake tract downstream of a junction with an exhaust gas recirculation unit. A carbon dioxide concentration of an air mixture intake is thus determined and used to contribute to a precise exhaust gas recirculation.

In some embodiments, a second sound conversion unit is operated for sending and receiving a third sound signal at a predefined third frequency.

A third propagation time of the third sound signal is determined. On the basis of the first propagation time and the third propagation time, a second characteristic value is determined, which is representative of a mass flow of the fluid mixture.

Due to the additional sound conversion unit an additional frequency range is covered, for example, in which the effect of the sound dispersion occurs in a measurable way. This means that, for example, the concentration of the constituent of the fluid mixture can be determined with a high level of reliability.

If the concentration of the constituent of a flowing fluid mixture is determined and a first component of a first main radiation direction of the first sound signal is oriented in the opposite direction to a first component of a third main radiation direction of the third sound signal and the first component of the first main radiation direction and the first component of the third main radiation direction are parallel to a main flow direction of the fluid mixture, then such an arrangement enables a simultaneous determination of a mass flow.

For example, the second sound conversion unit is additionally operated for sending and receiving a fourth sound signal at a predefined fourth frequency, the fourth propagation time of which is determined. On the basis of the fourth propagation time a redundant characteristic value can be determined, which is representative, for example, of the first characteristic value or of the second characteristic value, which contributes to a high reliability of the method.

Some embodiments may include an apparatus for determining a concentration of a constituent of a fluid mixture in a fluid chamber, which comprises a first sound conversion unit which is designed for sending and receiving a first sound signal and a second sound signal.

The apparatus also comprises a control unit which is designed for carrying out a method in accordance with the first aspect. This enables a reliable determination of the concentration of the constituent of the fluid mixture. Such an apparatus is also robust and inexpensive to produce.

A transmitter for sending a respective sound signal of the first sound conversion unit can be arranged, for example, in an assembly with a corresponding receiver for receiving the respective sound signal, or arranged spatially separated from the corresponding receiver.

In some embodiments, the first sound conversion unit comprises at least one first sound transducer. This facilitates an inexpensive, space-saving arrangement in which the at least one first sound transducer is operated, for example, as a transmitter at one time and as a receiver at another time.

For example, the first sound conversion unit has a single first sound transducer which is designed, for example, as a CMUT-sound transducer or as a piezoelectric sound transducer, and which is designed for sending and receiving the first and second sound signal. Alternatively, the first sound conversion unit has, for example, one first sound transducer each, which is designed for sending and receiving the first sound signal or the second sound signal respectively. For example, the first sound conversion unit is designed as a MEMS-module, which comprises two CMUT sound transducers.

Such a MEMS-module, in contrast to a plastic circuit board, can comprise for example up to four sound transducers on a single piece of silicone and can be produced inexpensively and in a space-saving design.

In some embodiments, the at least one first sound transducer is designed as a CMUT. CMUTs are micromechanically produced ultrasonic transducers, whose energy conversion is based on a change in their capacitance.

Due to its short decay time, a CMUT designed sound transducer (CMUT sound transducer) is ready-to-receive faster than a piezoelectric sound transducer, so that a measuring path can be kept short. In an advantageous manner, the short predefined distance enables a compact design. In addition, CMUT sound transducers are characterized by a particularly broad bandwidth, high temperature resistance and a cost-effective and space-saving production.

In some embodiments, the apparatus has a reflector element. The reflector element is also designed to reflect the first sound signal and the second sound signal in each case in such a way that the first sound conversion unit receives the reflected first sound signal and the reflected second sound signal. This enables a particularly cost-effective and space-saving arrangement for determining the concentration of the constituent of the fluid mixture.

In some embodiments, the apparatus comprises a second sound conversion unit which is designed for sending and receiving a third sound signal. For example, the second sound conversion unit is additionally designed for sending and receiving a fourth sound signal at a predefined fourth frequency. The additional second sound conversion unit covers, for example, an additional frequency range. This means that, for example, the concentration of the constituent of the fluid mixture can be determined with a higher level of reliability.

The fluid mixture has, for example, a main flow direction.

For example, a first main radiation direction of the first sound signal and a third main radiation direction of the third sound signal each have a first component, oriented in opposite directions to one another and parallel to the main flow direction of the fluid mixture. In this case, a simultaneous determination of a mass flow of the fluid mixture in the main flow direction is enabled.

In some embodiments, the second sound conversion unit comprises at least one second sound transducer.

In some embodiments, the at least one second sound transducer is designed as a CMUT.

In an intake tract of a combustion engine, downstream of a junction with an exhaust gas recirculation unit, an intake manifold ASR with a fluid chamber FR is arranged (FIG. 1).

A fluid mixture FG flows through the fluid chamber FR and is passed into a combustion chamber of the combustion engine. In the fluid chamber FR an apparatus for determining a concentration of a constituent B of the fluid mixture FG is arranged, for example to control exhaust-gas recirculation.

The apparatus has a first sound conversion unit SE1, which comprises a first transmitter S1 for sending a first sound signal SS1 at a predefined first frequency F1, and a second transmitter S2 for sending a second sound signal SS2 at a predefined second frequency F2. The first sound conversion unit SE1 also comprises a first receiver E1 for receiving the first sound signal SS1 and a second receiver E2 for receiving the second sound signal SS2. For example, the first sound conversion unit SE1 comprises at least one first sound transducer SW1 for this purpose. For example, the at least one first sound transducer SW1 in the fluid chamber FR is arranged on a wall W of the intake manifold ASR, so that a main radiation direction of the first transmitter S1 and of the second transmitter S2 is directed away from the wall W of the intake manifold ASR, into the fluid chamber FR.

The first receiver E1 and the second receiver E2 are arranged, for example, opposite each other on the wall W of the intake manifold ASR at a predefined distance A from the first transmitter S1 and from the second transmitter S2 and facing towards the first transmitter S1 and the second transmitter S2.

Some embodiments may include a second sound conversion unit SE2, which comprises a third transmitter S3 for sending a third sound signal SS3 at a predefined third frequency F3, and a fourth transmitter S4 for sending a fourth sound signal SS4 at a predefined fourth frequency F4. The second sound conversion unit SE2 also comprises a third receiver E3 for receiving the third sound signal SS3 and a fourth receiver E4 for receiving the fourth sound signal SS4. For example, the second sound conversion unit SE2 comprises at least one second sound transducer SW2 for this purpose.

In this context, use is made of the fact that a sound dispersion effect occurs to different extents, depending on the fluid mixture FG and the concentration of the constituent B in the fluid mixture FG.

The fluid mixture FG comprises, for example, oxygen and carbon dioxide. The first sound signal SS1 at the predefined first frequency F1, for example, has a first sound velocity C1 in the fluid mixture FG. The second sound signal SS2 at the predefined second frequency F2, for example, has a second sound velocity C2 in the fluid mixture FG.

Figure 2:
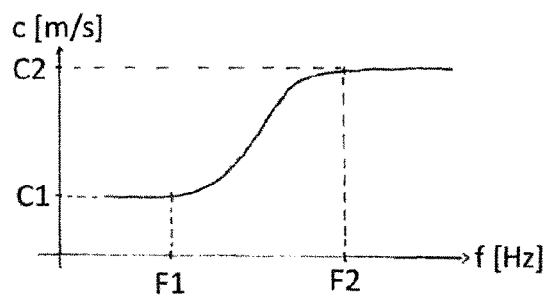
FIG. 2 an example of a sound dispersion curve.

Depending on the carbon dioxide concentration in the fluid mixture FG, a difference of the first sound velocity C1 relative to the second sound velocity C2 can be up to 10% of the first sound velocity C1, largely independent of an oxygen concentration or a concentration of other fluids in the fluid mixture FG. A sound dispersion curve of this kind for a given carbon dioxide concentration is shown in FIG. 2.

To determine the sound velocities C1, C2 the device is also designed to determine a respective propagation time of the sound signals SS1, SS2 in the fluid chamber FR. For example, the apparatus is also designed to determine a sound velocity of the third sound signal SS3 and the fourth sound signal SS4, so that in each case a sound velocity is determined for two sound signals of different frequencies, from which the carbon dioxide concentration can be deduced.

For example, the first predefined frequency F1 is equal to the third predefined frequency F3. In addition, for example, the second predefined frequency F2 is equal to the fourth predefined frequency F4, so that the at least one first sound transducer SW1 and the at least one second sound transducer SW2 are identically designed.

The sound transducers SW1, SW2 are designed for example as capacitive, micromachined ultrasonic transducers (CMUT, hereafter CMUT sound transducers).

CMUT sound transducers are ultrasonic transducers, whose energy conversion is based on a change in their capacitance. A CMUT sound transducer comprises a cavity in a silicon substrate, which serves as a first electrode and is covered by a thin, metallized membrane which serves as the second electrode. If an alternating current signal is applied to the two electrodes, the membrane is excited into vibration and ultrasonic waves are generated, so that the CMUT sound transducer operates as a transmitter. If ultrasonic waves strike the membrane, a change occurs in the capacitance of the CMUT sound transducer, an alternating signal is generated and the CMUT sound transducer operates as a receiver.

Figure 3:
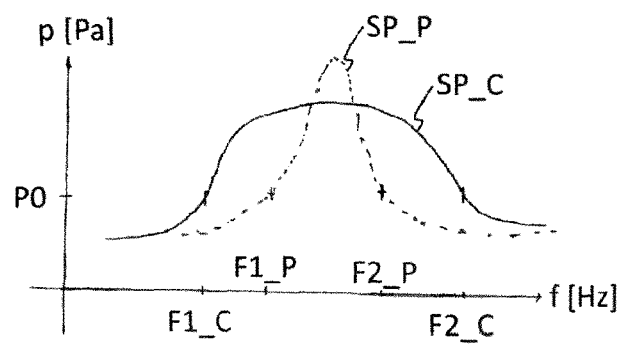
FIG. 3 a frequency spectrum of a CMUT sound transducer and a frequency spectrum of a piezoelectric sound transducer, FIG. 4a an embodiment of a first module for determining the concentration of the constituent of the fluid mixture in the fluid chamber, according to teachings of the present disclosure.

The geometry of a CMUT sound transducer, in particular the size of its base surface, defines a frequency spectrum of the sound transducer. FIG. 3 shows a frequency spectrum SP_C of an exemplary CMUT sound transducer. For comparison purposes, a frequency spectrum SP_P of an exemplary piezoelectric sound transducer is also shown by a dashed line. In order to ensure a reliable determination of the carbon dioxide concentration, a minimum sound pressure P0 of the sound signal is required. The CMUT sound transducer reaches the minimum sound pressure P0 at a first frequency F1_C and exceeds this up to a second frequency F2_C. The frequency spectrum SP_P of the piezoelectric sound transducer by contrast is substantially narrower, so that a first frequency F1_P, at which the piezoelectric sound transducer reaches the minimum sound pressure P0 is greater than the first frequency F1_C, for example, and a second frequency F2_P, up to which the minimum sound pressure P0 is exceeded is lower than the second frequency F2_C, for example.

Due to the ability of the CMUT sound transducer to be tuned over a broad frequency range between F1_C and F2_C, at which the required minimum sound pressure P0 is reached, it is possible to induce a measurable level of the sound dispersion used for determining the carbon dioxide concentration with only a single CMUT sound transducer. For example, the first frequency F1_C of the CMUT sound transducer is equal to the predefined first frequency F1 of the first sound signal SS1 and the second frequency F2_C of the CMUT sound transducer is equal to the predefined second frequency F2 of the second sound signal SS2.

Instead of two separate sound transducers in each case therefore, the first transmitter S1 and the second transmitter S2, for example, may be implemented in a single first sound transducer SW1 and the third transmitter S3 and the fourth transmitter S4 may be implemented in a single second sound transducer SW2.

In the event that the predefined first frequency F1 is equal to the predefined third frequency F3 and the predefined second frequency F2 is equal to the predefined fourth frequency F4, the receivers E1, E2 and transmitters S3, S4 are advantageously implemented for example in a first assembly BE1 designed as a CMUT sound transducer, and the transmitters S1, S2 and receivers E3, E4 are implemented in a second assembly BE2 designed as a CMUT sound transducer (FIG. 1).

Figure 4A:
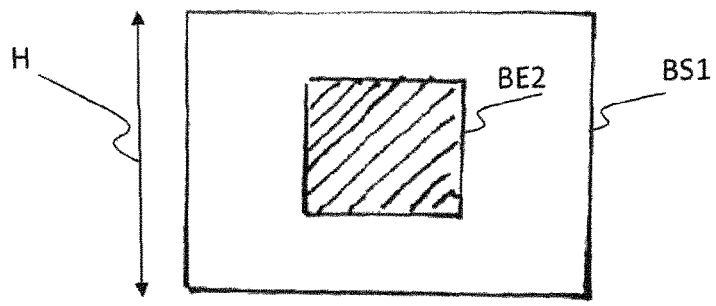

FIG. 4a shows a first module BS1 with a height H, which is designed for example as a MEMS module and whose height H is 1 mm.

Figure 4B:
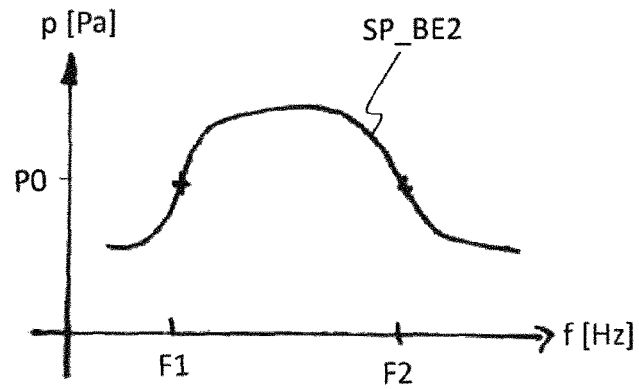

The first module BS1 comprises the second assembly BE2, which is designed for example as a CMUT sound transducer and whose frequency spectrum SP_BE2 is shown in FIG. 4b. The frequency spectrum of SP_BE2 reaches the minimum sound pressure P0 at the predefined first frequency F1 of the first sound signal SS1 and up to the predefined second frequency F2 of the second sound signal SS2.

Figure 5A:
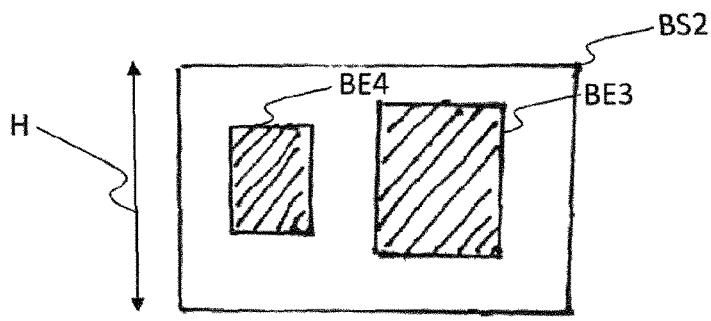
FIG. 5a an embodiment of a second module for determining the concentration of the constituent of the fluid mixture in the fluid chamber, according to teachings of the present disclosure.
Figure 5B:
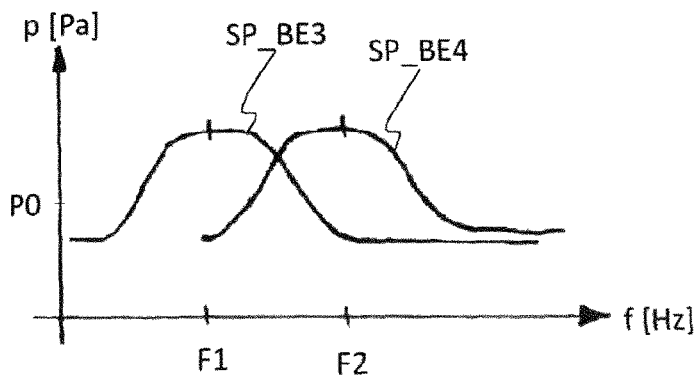

Alternatively, in FIG. 5a a second module BS2 with the height H is shown, which similarly to the first module BS1 is designed for example as a MEMS module, whose height H is 1 mm. The second module BS2 comprises a third assembly BE3 and a fourth assembly BE4, which are designed for example as CMUT sound transducers and whose frequency spectrum SP_BE3, SP_BE4 are each shown in FIG. 5b.

By means of a larger base surface of the fourth assembly BE4 compared to the second assembly BE2, the frequency spectrum SP_BE4 of the fourth assembly BE4 is shifted to a lower frequency range, so that the frequency spectrum SP_BE4 reaches a maximum, for example, at the predefined first frequency F1. By means of a larger base surface of the third assembly BE3 compared to the second assembly BE2, the frequency spectrum SP_BE3 of the third assembly BE3 is shifted to a higher frequency range, so that the frequency spectrum SP_BE3 reaches a maximum, for example, at the predefined second frequency F2.

By means of this type of arrangement, a frequency spectrum of the second module BS2 at the minimum sound pressure P0 is particularly broad. Furthermore, a sound pressure at the predefined first frequency F1 and the predefined second frequency F2 is a maximum. This contributes to a reliable determination of the concentration of the constituent B in the fluid mixture FG.

Figure 6:
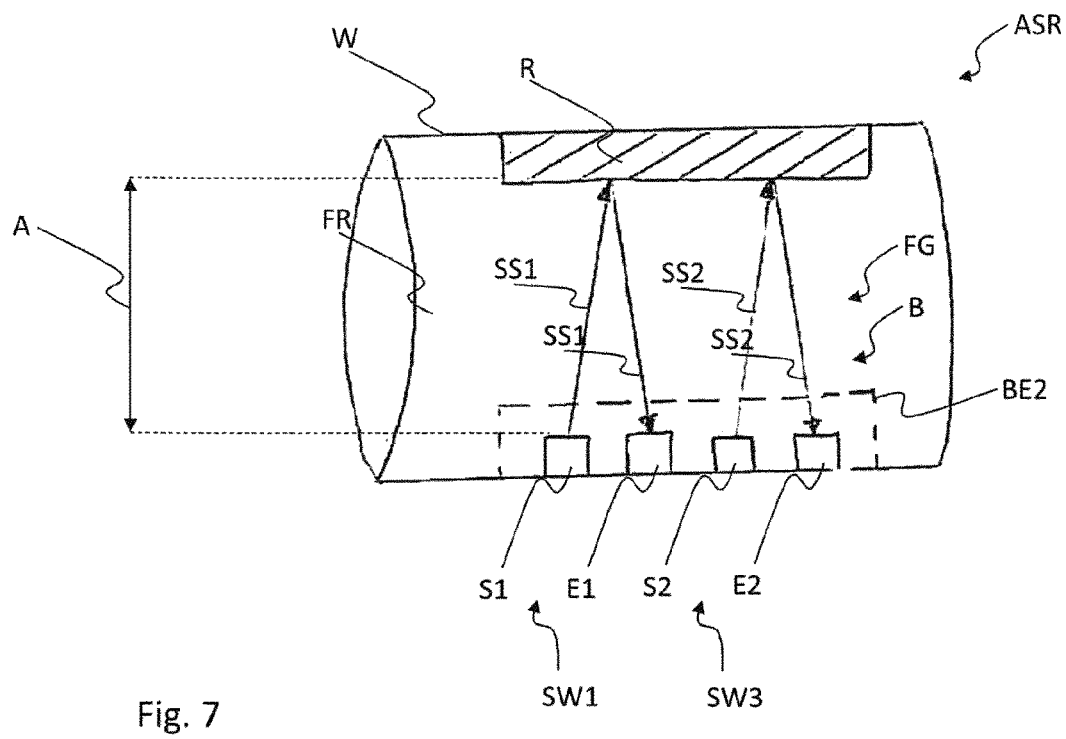
FIG. 6 a second exemplary embodiment of the apparatus for determining the concentration of the constituent of the fluid mixture in the fluid chamber, according to teachings of the present disclosure.

FIG. 6 shows a second exemplary embodiment of an apparatus for determining the concentration of the constituent B of the fluid mixture FG in the fluid chamber FR, that differs from the first exemplary embodiment in FIG. 1 in that instead of a first assembly BE1 a reflector element R is arranged, for example, on the wall W of the intake manifold ASR, so that the first sound signal SS1 of the first transmitter S1 is reflected onto the first receiver E1 and the second sound signal SS2 of the second transmitter S2 is reflected onto the second receiver E2.

The reflector element R in this case is arranged at the predefined distance A from the transmitters S1, S2. Such an arrangement enables a reliable determination of the concentration of the constituent B in the fluid mixture FG in the fluid chamber FR combined with an inexpensive production.

Figure 7:
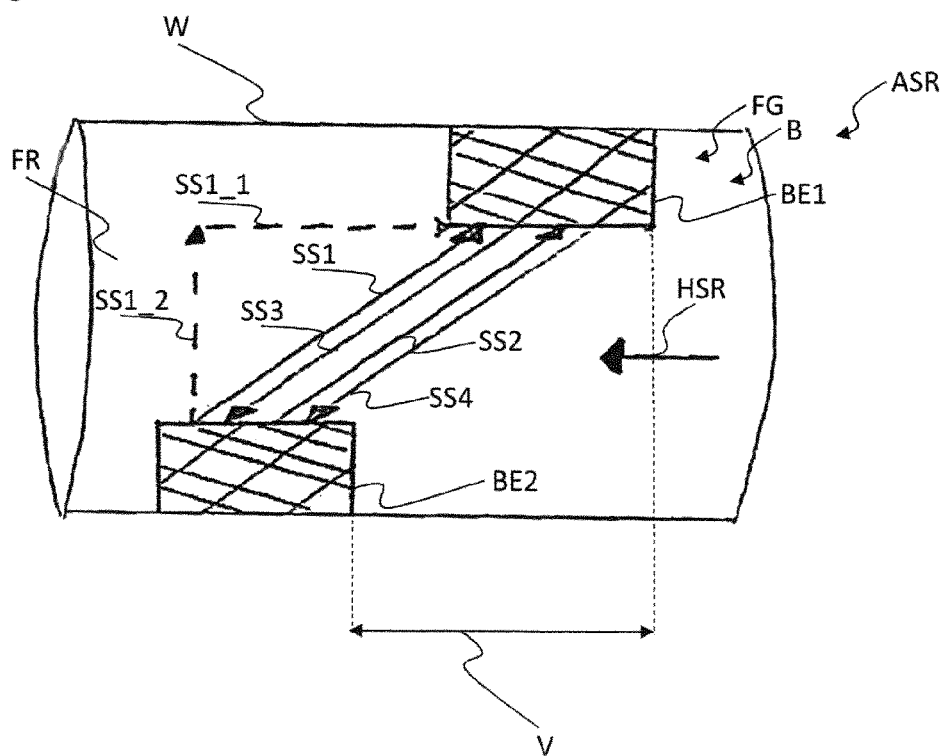
FIG. 7 a third exemplary embodiment of the apparatus for determining the concentration of the constituent of the fluid mixture in the fluid chamber, according to teachings of the present disclosure.

FIG. 7 shows a third exemplary embodiment of an apparatus for determining the concentration of the constituent B of the fluid mixture FG in the fluid chamber FR, that differs from the first exemplary embodiment of FIG. 1 in that the second assembly BE2 is arranged with an offset V relative to the first assembly BE1 in the main flow direction HSR of the fluid mixture FG.

The sound signals SS1 and SS2 each have a first component opposite to the main flow direction HSR. The sound signals SS3 and SS4 each have a first component in the main flow direction HSR. For example, the first sound signal SS1 comprises a first component SS1_1 against the main flow direction HSR and a second component SS1_2 perpendicular to the main flow direction HSR. For example, the predefined first frequency F1 is equal to the predefined third frequency F3, so that by means of a different propagation time of the first sound signal SS1 and the third sound signal SS3 a mass flow of the fluid mixture FG can be determined free from sound dispersion.

Analogously, for example, the predefined second frequency F2 is equal to the predefined fourth frequency F4, so that by means of a different propagation time of the second sound signal SS2 and the fourth sound signal SS4 a mass flow of the fluid mixture FG can be determined free from sound dispersion.

Figure 8:
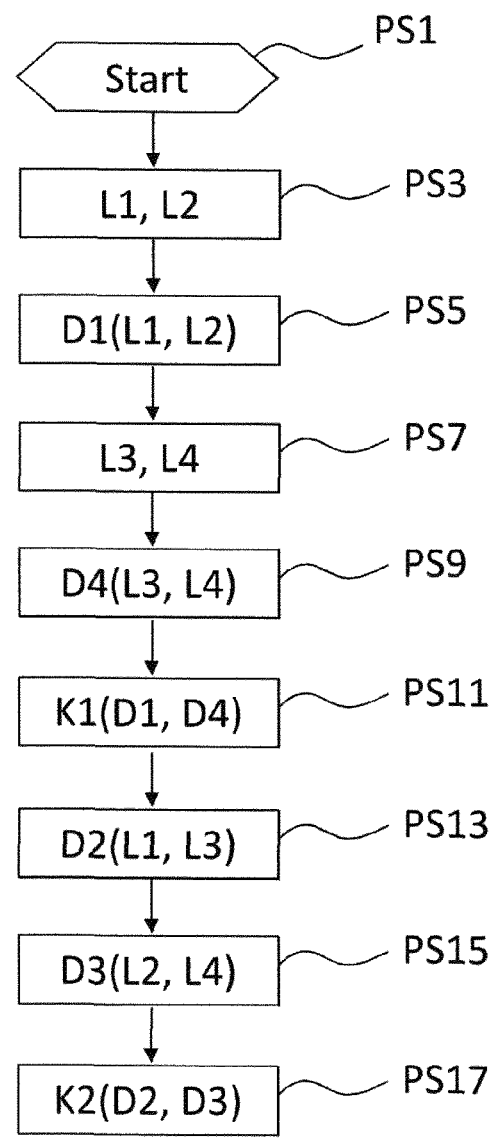
FIG. 8 a flow diagram of a program for implementing a method for determining the concentration of the constituent of the fluid mixture in the fluid chamber.

The apparatus of FIGS. 1, 6 and 7 comprises a control unit, not shown in detail, in the data and program memory of which a program for determining the concentration of the constituent B of the fluid mixture FG is stored, which is described in greater detail hereafter by reference to the flow diagram of FIG. 8.

The program is launched in a program step PS1, in which variables are initialized, for example.

In a program step PS3 a first propagation time L1 of the first sound signal SS1 and a second propagation time L2 of the second sound signal SS2 is determined. The program is then continued in a program step PS5.

In the program step PS5, on the basis of the first propagation time L1 and the second propagation time L2 a first difference D1 in the propagation times L1, L2 is determined. The program is continued in a program step PS7.

In the program step PS7 a third propagation time L3 of the third sound signal SS3 and a fourth propagation time L4 of the fourth sound signal SS4 is determined. The program is then continued in a program step PS9. In the program step PS9, on the basis of the third propagation time L3 and the fourth propagation time L4, a fourth difference D4 in the propagation times L3, L4 is determined. The program is then continued in a program step PS11.

In the program step PS11, on the basis of the first difference D1 and the fourth difference D4 a first characteristic value K1 is determined, which is representative of the concentration of the constituent B of the fluid mixture FG. The program is continued in a program step PS13.

In the program step PS13, on the basis of the first propagation time L1 and the third propagation time L3, a second difference D2 in the propagation times L1, L3 is determined. The program is continued in a program step PS15.

In the program step PS15, on the basis of the second propagation time L2 and the fourth propagation time L4, a third difference D3 in the propagation times L2, L4 is determined. The program is continued in a program step PS17.

In the program step PS17, on the basis of the first difference D2 and the third difference D3 a second characteristic value K2 is determined which is representative of a mass flow of the fluid mixture FG.

What is claimed is:

1. A method for controlling an internal combustion engine, the method comprising:
   sending and receiving a first sound signal with a first sound conversion unit at a predefined first frequency;
   sending and receiving a second sound signal with the first sound conversion unit at a predefined second frequency;
   measuring a first propagation time of the first sound signal;
   measuring a second propagation time of the second sound signal;
   calculating a first characteristic value based at least in part on the first propagation time and the second propagation time, the first characteristic value representative of the concentration of the constituent of the fluid mixture;
   sending and receiving a third sound signal with a second sound conversion unit at a predefined third frequency;
   measuring a third propagation time of the third sound signal;
   calculating a second characteristic value based at least in part on the first propagation time and the third propagation time, the second characteristic value representative of a mass flow of a fluid mixture through an intake tract with an exhaust gas recirculation unit; and
   controlling an exhaust gas recirculation based on the second characteristic value calculated.

2. The method as claimed in claim 1, wherein the first characteristic value is representative of a carbon dioxide concentration in the intake tract.

3. The method as claimed in claim 1, further comprising the intake tract arranged downstream of a junction with an exhaust gas recirculation unit.

4. An apparatus for controlling an internal combustion engine, the apparatus comprising:
   a first sound conversion unit for sending and receiving a first sound signal and a second sound signal;
   a second sound conversion unit for sending and receiving a third sound signal; and
   a control unit operating to:
      measure a first propagation time of the first sound signal;
      measure a second propagation time of the second sound signal;
      calculate a first characteristic value based at least in part on the first propagation time and the second propagation time, the first characteristic value representative of the concentration of the constituent of the fluid mixture;
      measure a third propagation time of the third sound signal; and
      calculate a second characteristic value based at least in part on the first propagation time and the third propagation time, the second characteristic value representative of a mass flow through an intake tract with an exhaust gas recirculation unit; and
      control an exhaust gas recirculation based on the second characteristic value calculated.

5. The apparatus as claimed in claim 4, wherein the first sound conversion unit comprises a sound transducer.

6. The apparatus as claimed in claim 5, wherein the sound transducer comprises a capacitive micromachined ultrasonic transducer (CMUT).

7. The apparatus as claimed claim 4, further comprising a reflector element to reflect the first sound signal and the second sound signal back to the first sound conversion unit.

8. The apparatus as claimed in claim 4, wherein the second sound conversion unit comprises a second sound transducer.

9. The apparatus as claimed in claim 8, wherein the second sound transducer comprises a capacitive micromachined ultrasonic transducer (CMUT).

* * * * *